United States Patent [19]

Lutenegger

[11] Patent Number: 4,474,066

[45] Date of Patent: Oct. 2, 1984

[54] PORTABLE VARIABLE EXPANSION TESTING DEVICE

[75] Inventor: Alan J. Lutenegger, Ames, Iowa

[73] Assignee: Iowa State University Research Foundation, Inc., Ames, Iowa

[21] Appl. No.: 477,083

[22] Filed: Mar. 21, 1983

[51] Int. Cl.³ .............................................. G01N 3/10
[52] U.S. Cl. ........................................ 73/790; 73/819
[58] Field of Search .................. 73/862.58, 822, 823, 73/825, 818, 819, 790

[56] References Cited

U.S. PATENT DOCUMENTS

| | | | |
|---|---|---|---|
| 1,998,722 | 4/1935 | Hveem | 265/14 |
| 3,054,286 | 9/1962 | Karol | 73/825 X |
| 3,608,367 | 9/1971 | Karol | 73/825 |
| 3,854,328 | 12/1974 | Schmidt | 73/822 X |
| 4,047,425 | 9/1977 | Handy et al. | 73/822 |
| 4,122,704 | 10/1978 | Lutenegger et al. | 73/822 |

FOREIGN PATENT DOCUMENTS 436265 10/1974 U.S.S.R. .............................. 73/825

Primary Examiner—Jerry W. Myracle
Attorney, Agent, or Firm—Zarley, McKee, Thomte, Voorhees & Sease

[57] ABSTRACT

The present invention is a portable testing device for directly measuring developed lateral pressure and displacement induced on a material by a vertically applied load. The testing device comprises a thin walled cylindrical sleeve-like receptacle which is capable of lateral expansion in response to a vertically applied force on the material contained in the receptacle. A pressure sensing cylinder engages the expandable receptacle wall and has a stress gauge operatively connected thereto for sensing the pressure within the sensing cylinder. A strain gauge is also connected to the sensing piston for registering lateral displacement thereof. The improvement on this device comprises a control cylinder for regulating the pressure within the sensing cylinder. The control cylinder includes a control piston and threaded screw for adjustment of the control piston position within the control cylinder. The control cylinder is in fluid communication with the sensing cylinder and with the stress gauge.

12 Claims, 4 Drawing Figures

PORTABLE VARIABLE EXPANSION TESTING DEVICE

BACKGROUND OF THE INVENTION

The lateral stress induced upon soil subjected to compressive forces is an important and fundamental aspect of engineering behavior of the soil particularly in relationship to the stress on retaining walls and to the soil-bearing capacity under loads. Being able to monitor the ratio of lateral stress to vertical stress is important when structures are constructed upon the soil. Being able to assess this ratio and to evaluate its effect for a given soil sammple is helpful in determining whether or not the soil can properly withstand applied vertical pressure. The ratio of lateral to vertical stress is known as the Rankine stress ratio and is designated "K".

An example of a prior device for measuring lateral pressure induced on the soil by a vertically applied compressive force is shown in U.S. Pat. No. 4,122,704. This device is limited to performing only one soil test, the standard lateral stress test, which measures continuously increasing lateral pressures on the soil when that soil is subjected to various vertical pressures. The device of U.S. Pat. No. 4,122,704 can not perform other tests such as the constant lateral stress test and the constant lateral strain test. These two additional tests are important to an effective analysis of the stress-strain characteristics of the soil.

The constant lateral stress test involves keeping the lateral pressure constant during exposure of the sample to a number of different vertical pressures. Keeping the horizontal pressure constant permits measurement of the horizontal displacement of the soil sample in response to various vertical pressures. The device of U.S. Pat. No. 4,122,704 does not include means for maintaining a constant horizontal pressure in response to various vertical pressures.

Similarly, the device of U.S. Pat. No. 4,122,704 does not provide means for holding the soil sample against horizontal displacement during exposure to various vertical pressures. This capability is essential to performing the constant strain test where during exposure to various vertical pressures the lateral displacement is held constant and measurements of lateral pressures are taken.

Therefore, a primary objective of the present invention is the provision of an improved device for determining the stress-strain relationships of soil.

A further objective of the present invention is the provision of a device capable of yielding accurate results when performing constant lateral strain tests, constant lateral stress tests, and standard lateral stress tests.

A further objective of the present invention is the provision of an apparatus for testing the stress-strain characteristics of soil which may be used either on undisturbed field samples or soil samples which have been subjected to pre-treatment in order to simulate anticipated environmental conditions.

A further objective of the present invention is the provision of a soil testing device which is portable so that the test may be conducted at a field site on samples obtained therefrom.

A further object of the present invention is the provision of a device which is economical to manufacture, durable in use, and efficient in operation.

SUMMARY OF THE INVENTION

The present invention provides a device which can perform the standard stress test, the constant stress test, and the constant strain test. During the standard stress test, the device permits both the lateral pressure and the lateral displacement to vary in response to different vertical pressures. During the constant stress test it permits the lateral pressure to be held constant during the exposure to different vertical pressures, while at the same time permitting the lateral displacement to vary. During the constant strain test it permits the lateral displacement to be held constant so that lateral pressure responses can be observed during exposure to different vertical pressures.

The invention includes a receptacle for receiving the soil sample. The receptacle is cylindrical in shape and has a vertical slot in its cylindrical wall which permits the cylinder to expand laterally in response to pressure being applied to the sample. A circular plate is fit over the sample, and the circular plate is subjected to varying vertical pressures. In response to these vertical pressures the sample expands laterally and causes the split wall of the cylinder to expand laterally also.

Apparatus is attached to the two split sides of the cylindrical wall of the receptacle for sensing the lateral movement of the receptacle in response to lateral displacement of the soil sample. The sensing apparatus includes a pneumatic cylinder having a piston rod attached to one side of the split receptacle cylinder so that it moves laterally in response to lateral movement of the receptacle cylinder walls.

The sensing cylinder has a strain dial which is connected to the piston of the cylinder and which registers the lateral displacement of the piston of the cylinder. The sensing cylinder also has a pressure dial or stress dial which registers the fluid pressure within the cylinder. As the piston of the sensing cylinder is displaced the pressure within the cylinder increases thereby registering increasing pressures on the stress gauge.

The present invention also includes the provision of a hydraulic control system connected to the sensing cylinder for permitting adjustment of the pressure within the sensing cylinder. The control system comprises a screw and a handle attached to the piston of a closed hydraulic cylinder. As the screw handle is turned, the piston moves longitudinally within the cylinder. The cylinder is connected into the fluid circuitry of the sensing cylinder so that rotation of the screw handle causes adjustment of the pressure within the sensing cylinder.

By turning the screw handle in the control means of the present invention it is possible to maintain the stress gauge at a constant reading throughout the exposure of the soil sample to various vertical pressures within the receptacle. It is also possible by adjusting the handle of the control means to hold the strain gauge constant, thereby permitting the stress gauge to vary its reading in response to the vertical pressures applied to the soil sample.

Therefore the control means of the present invention permits the device to be used for accomplishing all of the tests described above. The standard test can be accomplished by leaving the control means alone and letting the stress and strain gauges react naturally to the vertical pressure applied to the soil sample. The constant stress test can be accomplished by adjusting the handle to maintain the stress gauge at a constant reading throughout exposure to various vertical pressures on the soil sample. The constant strain test can be accomplished by adjusting the handle so that the strain gauge remains at a constant reading throughout the test.

DETAILED DESCRIPTION OF THE DRAWINGS

Figure 1:
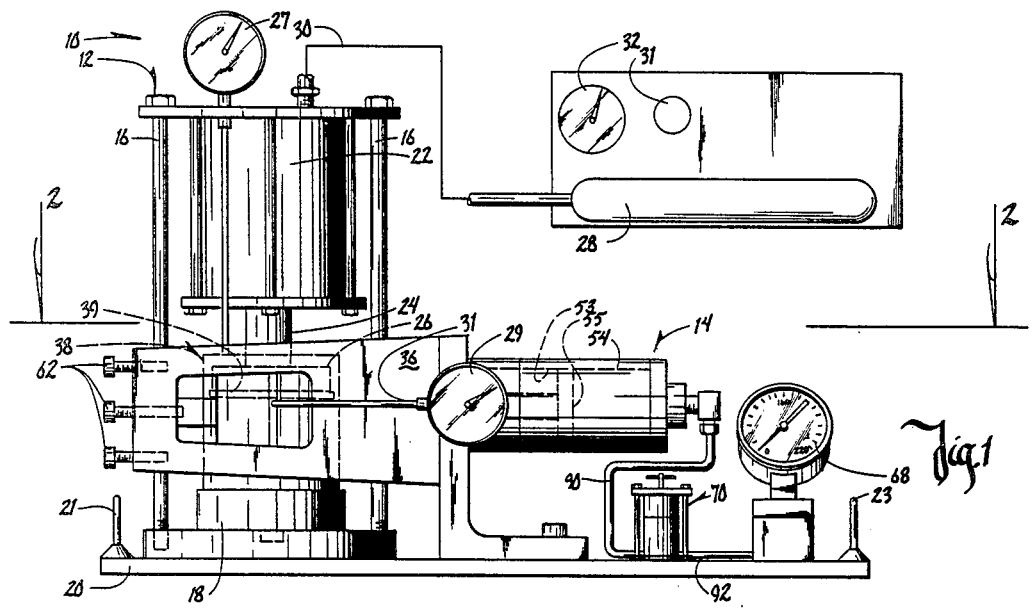
FIG. 1 is a side elevation view of the testing device of this invention.
Figure 2:
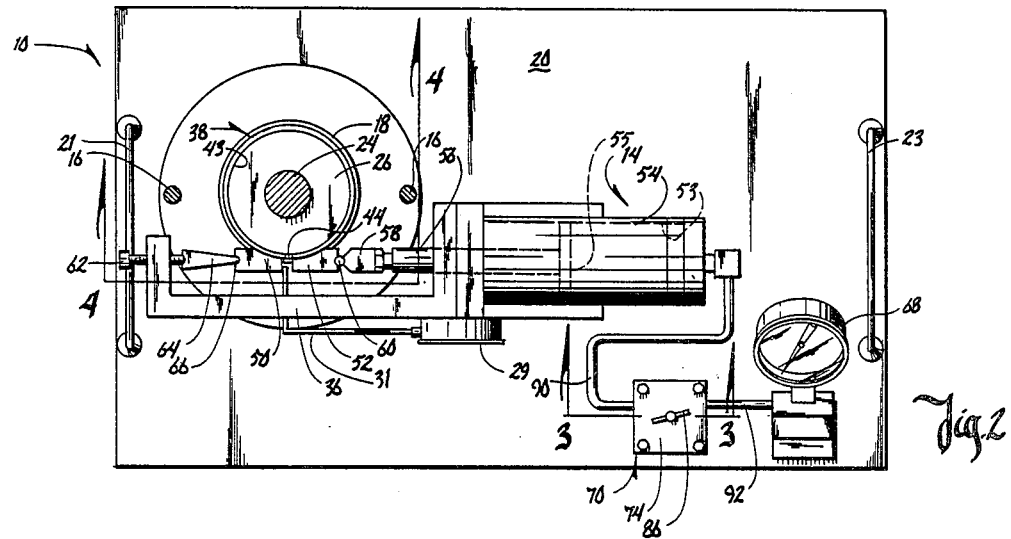
FIG. 2 is a sectional view of the device as seen on lines 2—2 of FIG. 1.

The continuous Rankine stress monitoring device 10 of FIGS. 1-2 generally comprises a load mechanism 12 and a lateral pressure measuring system 14 mounted on the base 20 having handles 21 and 23 secured thereto. Mechanism 12 comprises a pair of support rods 16 attached at their lower ends to a plate 18 positioned on the base 20. A loading cylinder 22 is attached to and supported by the upper ends of rods 16, and has a piston rod 24 extending downwardly therefrom which has a plate 26 secured to the lower end thereof. Vertical displacement gauge 27 measures vertical displacement of piston rod 24 and plate 26. The interior of cylinder 22 is fluidly connected to pressurized container of carbon dioxide 28 by line 30. The apparatus also includes a pressure regulator 31 and vertical pressure gauge 32. Thus, operation of the container 28 causes pressure to be supplied to the cylinder 22 thereby extending or lowering the cylinder rod 24.

The lateral pressure measuring system 14 of FIGS. 1-2 generally comprises a holding bracket 36 designed to support a cylindrical receptacle or sleeve 38. Receptacle 38 has an open top end and an open bottom end. Receptacle 38 has a slit 44 along its entire length parallel to the longitudinal axis of the cylindrical receptacle 38. Slit 44 defines side edge portions which are capable of yieldably expanding away from one another. Blocks 50 and 52 are secured to the exterior surface of the receptacle 38 adjacent the side edge portions.

A lateral pressure cylinder 54 is mounted on the holding bracket 36 in the manner illustrated in FIG. 1 and has cylinder rod 56 extending from the piston thereof. Rod 56 has an adapter 58 on its outer end adapted to engage a groove 60 on block 52. Adjustment screws 62 extend through bracket 36 and have an adapter 64 mounted on the inner ends thereof for engagement with a groove 66 in block 50 so as to prevent block 50 from moving. The cylinder 54 is provided with a fluid compartment 53 therein at one side of a puiston 55 contained therein. The fluid compartment 53 is in fluid communication with a pressure gauge 68 which registers the fluid pressure within compartment 53. A strain gauge 29 is connected to piston rod 56. Gauge 29 is also connected to block 50 by means of an L-shaped sensing rod 31. By sensing the relative movement between block 50 and piston rod 56, gauge 29 is able to register the lateral displacement of the two adjacent edges of soil receptacle 38.

When vertical pressure is applied to the material in receptacle 38, slot 44 expands. Because block 50 is held stationary by bracket 36 and scres 62, block 52 moves laterally away from block 50 in response to the vertical pressure. This movement of the block 52 towards the pressure cylinder 54 will cause the fluid in the compartment in the cylinder 54 to be compressed thereby causing the increased pressure therein to be registered on the gauge 68. Similarly the lateral displacement of slot 44 is registered on gauge 29.

Figure 3:
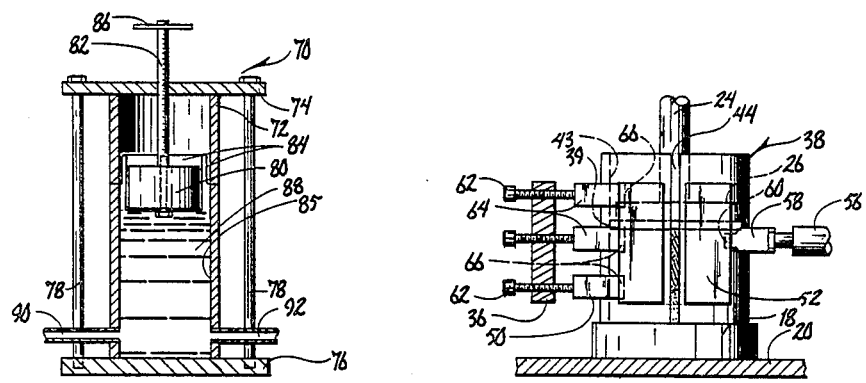
FIG. 3 is a sectional view taken along line 3—3 of FIG. 1.

The foregoing description relates to the device disclosed in U.S. Pat. No. 4,122,704. The present invention contemplates the use of a hydraulic control system 70 connected in communication with pressure cylinder 54, and pressure gauge 68. This control system may be a simple hydraulic hand pump, but preferably should be constructed of a screw-pump mechanism as shown in FIG. 3.

Hydraulic control system 70 comprises a closed hydraulic cylinder 72 mounted between upper and lower end plates 74 and 76, respectively, by elongated bolt members 78. A piston 80 is mounted on a rod 82 which is threadably received by upper end plate 74 and is secured to a bellofram diaphram 84 which is secured to the hydraulic cylinder inner wall 85. The diaphramm 84 provides a sealing engagement between piston 80 and the cylinder wall 85. A handle 86 is mounted on the upper end of threaded rod 82 for vertical control of piston 80. Hydraulic fluid 88 is contained within the hydraulic cylinder 72. Hydraulic control system 70 is in fluid communication with pressure cylinder 54 via hydraulic line 90 and is in fluid communication with pressure gauge 68 via hydraulic line 92. Lower end plate 76 is secured to base 20 of the device 10.

Figure 4:
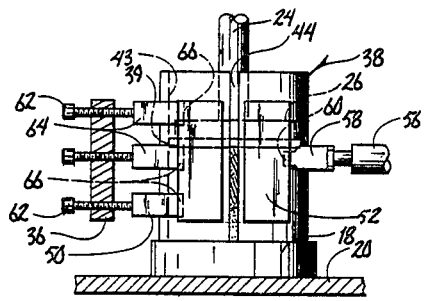
FIG. 4 is a sectional view taken along line 4—4 of FIG. 2.

In operation, a soil sample is placed within cylindrical receptacle 38 with plate 18 being received by the lower open end of the receptacle 38. A top closure member 39 is placed within cylindrical sleeve 38 directly on top of the soil sample. A downward vertical pressure is applied against the top closure member and correspondingly on the soil sample by plate 26 of loading mechanism 12. The compressive force cause an induced lateral pressure on the soil sample and correspondingly on the lateral wall surface of the cylindrical sleeve 38. Block 50 is prevented from lateral movement by means of a holding bracket 36 and screws 62. Block 52 is movable to the right as viewed in FIG. 4 in response to the expansion of slot 44. This causes piston 55 to move to the right which results in an increased pressure being registered on stress gauge 68. At the same time strain gauge 29 registers a change in lateral displacement.

In a standard or continuously increasing lateral stress test, threaded rod 82 of the hydraulic control system 70 is left untouched. The induced lateral pressure resulting from the downnward vertical force causes expansion of sleeve 38 transverse to its longitudinal axis with the result being that the width of the slit 44 is increased. Since block 50 is stationary, the edge portion adjacent block 50 is stationary and the edge portion adjacent block 52 moves laterally with respect to the opposite edge portion as the width of slit 44 increases, thus causing compression of the fluid in the compartment in cylinder 54 which is registered on the pressure gauge 68 to provide a reading thereon. The lateral displacement of block 50 is registered on gauge 29.

To conduct a constant lateral stress test, in which compressive forces are increased while the lateral stress is held constant, pressure gauge 68 is controlled by raising or lowering piston 80 within hydraulic cylinder 72 via threaded rod 82 so that the reading on gauge 68 is held constant. This is analogous to performing a more conventional triaxial shear test in which lateral stress is held constant during vertical loading. By testing a number of samples, each with varying values of lateral stress, the familiar Mohr-Coulomb shear strength envelope may be obtained.

The device of the present invention may also conduct a third test, the constant lateral strain test, in which vertical compressive forces are applied to the sample while maintaining a constant lateral strain or lateral displacement. During this test, piston 80 is raised or lowered within hydraulic cylinder 72 to the extent which is necessary to maintain a constant reading on strain gauge 29. Readings are then taken from stress gauge 68 to show the variation in stress when the strain is held constant. This test is important where there is a need to simulate anticipated field conditions by allowing the test sample to deform a specified amount and simultaneously measuring the corresponding lateral stresses which develop due to increasing applied vertical load. For example, a retaining system may be allowed to deflect a certain amount before it attains complete rigidity, after which an increase in vertical load on the back fill results in an increase in lateral stress.

A special instance of the constant lateral strain test when no lateral displacement is premitted at all in the test sample during vertical loading. This is known as the zero lateral strain test. The ratio of the lateral stress required to maintain the zero lateral strain position to the applied load is called $K_o$. The value of $K_o$ is an important geotechnical characteristic and is used in pile design, retaining wall design, and other construction projects.

The improvement of the portable variable expansion testing device provides a simple means of conducting various tests necessary to develop the stress-strain relationships in soil. These relationships can be computed from the various gauge readings. The improved device allows precise control of the lateral restraint by a simple feed-back system connected in series with the closed hydraulic system 70.

Variations to the hydraulic control system 70 may include using an air-oil system, controlled by compressed gas and a pressure regulator, or a servo or electric screw mechanism to advance or back-off the piston 80 at a constant rate. Such an electrical screw mechanism may be desirable to perform constant rate lateral strain tests.

Thus, it can be seen that the device of the present invention accomplishes at least all of the stated objectives.

What is claimed is:

1. An improved testing device to measure the lateral displacement and pressure induced on a material by a vertically applied pressure of the type having a material holding receptacle which has side walls capable of lateral expansion in response to a vertically applied force on a material contained in said receptacle, sensing means for sensing lateral expansion of said sidewalls, said sensing means comprising a piston and cylinder, said piston engaging said sidewalls of said receptacle and being displaceable to change the fluid pressure within said cylinder in response to expansion of said sidewalls, a stress gauge operatively connected to said cylinder body for sensing and indicating fluid pressure within said cylinder, and a strain gauge connected to said piston for registering lateral displacement of said piston in response to expansion of said receptacle said walls; said improvement comprising:

adjustable control means connected to said cylinder and being capable of adjustment to cause a change in the fluid pressure within said cylinder whereby the readings registered on said stress gauge and said strain gauge may be adjusted to predetermined values.

2. The testing device of claim 1 wherein said control means comprises a frame, a fluid control cylinder mounted on said frame, a control piston in sealing engagement with the inner wall of said control cylinder, and means for adjusting the position of said control piston within said control cylinder.

3. The testing device of claim 2 wherein said adjustment means comprises a control piston rod threadably received by said frame and having a first end secured to said control piston and a second end extending externally from said frame, whereby rotation of said control piston rod will adjust the position of said control piston within said control cylinder.

4. The testing device of claim 2 wherein a bellofram diaphram provides sealing engagement between said control piston and said control cylinder inner wall.

5. An improved testing device for measuring the lateral displacement and pressure induced on a soil material in response to a vertical pressure of the type having a material holding receptacle which is capable of lateral expansion in response to a vertical applied force on the soil material contained in said receptacle, said receptacle having a vertically disposed slit along its entire length to define first and second vertically disposed edge portions, a generally closed fluid pressure system, means operatively connecting said fluid pressure system to said receptacle such that pressure in said system is increased in response to movement of said first edge portion with respect to said second edge portion during lateral expansion of said receptacle, and means for sensing the pressure within said fluid pressure system, wherein the improvement comprises:

control means in fluid communication with said closed fluid pressure system and with said pressure sensing means, said control means being adjustable to change its fluid pressure within said pressure system.

6. The testing device of claim 5 wherein said control means comprises a frame, a control cylinder mounted on said frame, a control piston in sealing engagement with the inner wall of said control cylinder, and means for adjusting the position of said control piston within said control cylinder.

7. The testing device of claim 6 wherein said adjustment means is a piston rod being threadably received by said frame and having a first end secured to said control piston, a spaced apart second end extending from said frame, and a longitudinal axis, whereby rotation of said piston rod about said longitudinal axis will adjust the position of said piston within said control cylinder.

8. The testing device of claim 6 wherein a bellofram diaphragm provides sealing engagement between said control piston and said control cylinder inner wall.

9. A soil testing device for testing a soil sample comprising:

a cylindrical receptacle for holding said soil sample, said receptacle having cylindrical side walls, said side walls having a vertical slit formed therein for permitting said side walls to expand laterally in response to increased pressure being exerted on said walls from within said receptacle;

vertical pressure power means for applying vertical pressure to said soil sample within said receptacle whereby said soil sample will in response exert lateral pressure on said receptacle walls and cause said receptacle walls to expand laterally;

sensing means for sensing the lateral expansion of said receptacle side walls, said sensing means comprising a sensing cylinder having a sensing piston mounted for reciprocating movement therein, sensing piston rod connected to said sensing piston and being engaged by said receptacle side wall whereby lateral expansion of said receptacle side wall will cause displacement of said sensing piston within said cylinder, said sensing cylinder having fluid therein which will compress in response to movement of said sensing piston within said cylinder;

a stress gauge connected to said sensing cylinder for registering the fluid pressure therein;

a strain gauge conntected to said sensing piston for registering the lateral displacement of said sensing piston;

control means connected in fluid communication with said sensing cylinder for adjusting the fluid pressure within said sensing cylinder.

10. A testing device according to claim 9 wherein said control means comprises a control cylinder and a control piston mounted for reciprocating movement within said control cylinder.

11. A testing device according to claim 10 wherein said control means further comprises selective adjustment means connected to said control piston for permitting selective adjustment of the position of said piston within said cylinder.

12. A testing device according to claim 11 wherein said selective adjustment means comprises a threaded rod threadably extending through said control cylinder and having one end attached to said control piston, the other end of said threaded rod extending outside said control cylinder.

* * * * *